United States Patent
Lewis et al.

(10) Patent No.: US 11,548,012 B2
(45) Date of Patent: Jan. 10, 2023

(54) PROCESS TO TREAT METAL OR MINERAL ORES AND COLLECTOR COMPOSITION THEREFOR

(71) Applicant: NOURYON CHEMICALS INTERNATIONAL B.V., Arnhem (NL)

(72) Inventors: Andrew Clist Lewis, Kållekärr (SE); Willem Hendrikus Baan, Nijbroek (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 308 days.

(21) Appl. No.: 16/756,875

(22) PCT Filed: Oct. 16, 2018

(86) PCT No.: PCT/EP2018/078179
§ 371 (c)(1),
(2) Date: Apr. 17, 2020

(87) PCT Pub. No.: WO2019/076858
PCT Pub. Date: Apr. 25, 2019

(65) Prior Publication Data
US 2021/0197210 A1    Jul. 1, 2021

(30) Foreign Application Priority Data
Oct. 20, 2017 (EP) ..................... 17197569

(51) Int. Cl.
*B03D 1/01* (2006.01)
*C02F 1/24* (2006.01)
(Continued)

(52) U.S. Cl.
CPC ............ *B03D 1/01* (2013.01); *C02F 1/24* (2013.01); *C02F 1/683* (2013.01); *C07C 253/18* (2013.01);
(Continued)

(58) Field of Classification Search
None
See application file for complete search history.

(56) References Cited

U.S. PATENT DOCUMENTS 2,166,093 A * 7/1939 Harwood ................. B03D 1/01
209/901
2,175,093 A * 10/1939 Ralston .................... B03D 1/01
209/901
(Continued)

FOREIGN PATENT DOCUMENTS

AU      2006210497 A1    8/2006
AU      2006317498 B2    5/2007
(Continued)

OTHER PUBLICATIONS

ISA EPO, International Search Report issued in International Application No. PCT/EP2018/078179, dated Dec. 11, 2018.

*Primary Examiner* — Clare M Perrin
(74) *Attorney, Agent, or Firm* — Lorenz & Kopf, LLP (57) ABSTRACT

A process to treat metal or mineral ores is disclosed. The metal or mineral ore is a metallic sulphide ore including copper, gold, platinum, silver, nickel, molybdenum, arsenic sulphides, cobalt, zinc, lead, tin, antimony, or combinations thereof with a collector composition including a dimeric fatty nitrile. The dimeric fatty nitrile is prepared by a process including reacting a dimer fatty acid with ammonia at a temperature between about 200° C. and about 400° C. to form a dimeric amide and removing water from the dimeric amide to form the dimeric nitrile. The present disclosure also provides a collector composition containing the dimeric fatty nitrile and at least one further collector or frother compound.

20 Claims, 3 Drawing Sheets

Copper recovery, grade curves for nitrile and xanthate collectors.

(51) Int. Cl.
  *C02F 1/68* (2006.01)
  *C07C 253/18* (2006.01)
  *C07C 255/00* (2006.01)
  *C02F 103/10* (2006.01)
  *C02F 101/20* (2006.01)
(52) U.S. Cl.
  CPC ...... *B03D 2201/02* (2013.01); *B03D 2203/02* (2013.01); *C02F 2101/20* (2013.01); *C02F 2103/10* (2013.01); *C07C 255/00* (2013.01)

(56) References Cited

U.S. PATENT DOCUMENTS

| | | | |
|---|---|---|---|
| 3,114,704 A | 12/1963 | Kauffman et al. | |
| 3,179,250 A | 4/1965 | Bunge et al. | |
| 4,678,562 A * | 7/1987 | Keys | B03D 1/006 252/61 |
| 6,231,784 B1 * | 5/2001 | Virnig | C22B 15/00 560/24 |
| 9,302,274 B2 | 4/2016 | Nagaraj | |
| 2011/0186299 A1 | 8/2011 | Pou et al. | |
| 2011/0190541 A1 | 8/2011 | Beillon et al. | |
| 2016/0369155 A1 * | 12/2016 | Angman | C09K 8/54 |
| 2020/0048735 A1 | 2/2020 | Lewis et al. | |

FOREIGN PATENT DOCUMENTS

| | | | |
|---|---|---|---|
| CA | 746971 A | 11/1966 | |
| CL | 20132965 A1 | 5/2014 | |
| CL | 20140985 A1 | 8/2014 | |
| CL | 20192665 A1 | 3/2020 | |
| EP | 0106787 A2 | 4/1984 | |
| WO | 2007059559 A1 | 5/2007 | |
| WO | WO-2007059559 A1 * | 5/2007 | ............... B03D 1/01 |
| WO | 2009113935 A1 | 9/2009 | |

\* cited by examiner

Fig. 1. Recovery, grade curves for nitrile collectors for a copper ore.

Fig. 2. Copper recovery, grade curves for nitrile and xanthate collectors.

Fig. 3. Gold recovery, grade curves for nitrile and xanthate collectors.

Fig. 4. Lead recovery, grade curves for nitrile collectors.

Fig. 5. Zinc recovery, grade curves for nitrile collectors.

Fig. 6. Copper ore treatment with dimeric nitrile collector, amine collector and mixture

PROCESS TO TREAT METAL OR MINERAL ORES AND COLLECTOR COMPOSITION THEREFOR

CROSS-REFERENCE TO RELATED APPLICATION

This application is a U.S. National-Stage entry under 35 U.S.C. § 371 based on International Application No. PCT/EP2018/078179, filed Oct. 16, 2018, which was published under PCT Article 21(2) and which claims priority to European Application No. 17197569.1, filed Oct. 20, 2017, which are all hereby incorporated in their entirety by reference.

TECHNICAL FIELD

The present disclosure relates to a process to treat metal or mineral ores, such as copper-containing, or sulfide ores and to collector compositions that are suitably used in such processes.

BACKGROUND

Froth flotation is a physico-chemical process used to separate mineral particles considered economically valuable from those considered waste. It is based on the ability of air bubbles to selectively attach on those particles that were previously rendered hydrophobic. The particle-bubble combinations then rise to the froth phase from where they are discharged from the flotation cell, whilst the hydrophilic particles remain in the flotation cell. Particle hydrophobicity is, in turn, induced by special chemicals called collectors. In direct flotation systems, it is the economically valuable minerals which are rendered hydrophobic by the action of the collector. Similarly, in reverse flotation systems, the collector renders hydrophobicity to those mineral particles considered waste. The efficiency of the separation process is quantified in terms of recovery and grade. Recovery refers to the percentage of valuable product contained in the ore that is removed into the concentrate stream after flotation. Grade refers to the percentage of the economically valuable product in the concentrate after flotation. A higher value of recovery or grade indicates a more efficient flotation system.

Metal ores, most prominently copper ores with associated gold, silver and platinum group metals (PGM) are routinely floated with xanthate, dithiophosphate, thionocarbamate, thiocarbamate, mercaptobenzylthiazole, monothiophosphate and dithiophosphinates. Xanthate has dominated the mineral industry for much of the twentieth century, but as the need to process difficult ores has become more urgent in recent times better collectors such as dithiophosphate have been developed. For example, when performing a flotation process for copper sulfide ores that contain a high amount of pyrite, a mix of propyl ethyl thiocarbonate and propyl methyl dithiophosphate is an example of a collector that can be used.

The copper processing industry uses a large quantity of gangue depressants like lime for depressing pyrite ($FeS_2$), sulfur dioxide and sulfites for depressing galena (PbS), cyanide salts for depressing sphalerite (ZnS) and pyrite, sodium hydrosulfite and sodium sulfides for depressing copper to float molybdenite ($MoS_2$).

It is not uncommon for process plants to add 1,000 g/t of lime as a depressant during a process to treat copper ores. It is well known that lime removes copper ions from solution, which can activate the surface of pyrite and other unwanted minerals. Lime also has been shown to make the surface of pyrite and other minerals more hydrophilic, therefore reducing the tendency to float.

U.S. Pat. No. 2,166,093 discloses that nitrile collectors are effective in floating copper ores but discloses the use of a compound having a single nitrile functional group with a hydrophobic aliphatic component of 10 or less carbons. U.S. Pat. No. 2,175,093 discloses the use of aliphatic dinitriles (of a general structure of CN—R—CN, wherein R is an alkylene group) as froth flotation agents in copper ore flotation.

WO 2007/059559 discloses a process to treat copper ores using a collector composition containing a nitrile compound. The nitrile compounds tested in the document are hexyl dinitrile and several alkyl mononitriles containing an alkyl chain of at least 4 carbon atoms. It was shown that 11 or more carbons in the hydrophobic component attached to a nitrile were more efficient in floating copper sulfide, Au, Ag and platinum group elements (PGE). Examples given for the hydrophobic component are derived from coconut and tallow fatty acids.

U.S. Pat. No. 3,114,704 discloses a process to treat phosphate ores (which are non-sulfidic ores) by performing a flotation process employing a nitrile pitch as a collector component that is for a major portion hydrogenated to an amine. U.S. Pat. No. 3,179,250 discloses the use of a hydrogenated nitrile pitch amine in floating phosphate-containing iron oxide ores (which are also non-sulfidic ores). CA 746971 discloses a process to treat phosphate ores employing several amines such as a hydrogenated nitrile pitch amine. As can be taken from WO2009/113935 in a nitrile pitch an amount of dimeric components is present. When hydrogenating a nitrile pitch the dimeric nitriles are converted to dimeric amines.

There is a continued need to find better collectors for metal or mineral ores, such as copper or sulfide ores, which is driven by the necessity to process ores of lower grade and ores containing gangue minerals which are difficult to separate from the metal (copper) or mineral and are detrimental to the refining processes and quality of the finished product.

SUMMARY

A method to treat metal or mineral ores is provided. The metal or mineral ore is a metallic sulphide ore including copper, gold, platinum, silver, nickel, monybdenum, arsenic sulphides, cobalt, zinc, lead, tin, antimony, or combinations thereof with a collector composition comprising a dimeric nitrile. The dimeric nitrile is obtainable by a process comprising: reacting a dimer fatty acid with ammonia at a temperature between about 200° C. and 400° C. to form a dimeric amide and removing water from the dimeric amide to form the dimeric nitrile.

A collector composition is also provided. The collector composition comprises, as component (a), from 1% by weight to 99% by weight of a dimeric nitrile compound obtainable by a process comprising: reacting a dimer fatty acid with ammonia at a temperature between about 200° C. and about 400° C. to form a dimeric amide; and removing water from the dimeric amide to form the dimeric nitrile compound. The collector composition further comprises, as component (b), from 1% by weight to 99% by weight of a collector selected from xanthates, dithiophosphates, thionocarbamates, thiocarbamates, alkynes, mercaptobenzylthiazoles, monothiophosphates, dithiophosphinates, hydroxamates, and combinations thereof or a frother selected from phenols, alkyl sulfates, C5-C8 cyclic alcohols, alkoxyalkanes, polypropylene glycol ethers, polyglycol ethers, polyglycol glycerol ethers, pyridine base, natural oils, mixed ethers, aldehydes and ketone co-products of oxo alcohol production, ethoxylated alcohols, and combinations thereof.

BRIEF DESCRIPTION OF THE DRAWINGS

The present disclosure will hereinafter be described in conjunction with the following drawing figures, wherein like numerals denote like elements, and.

DETAILED DESCRIPTION

The present disclosure provides an improved process to treat metal or mineral ores, such as copper, or sulfide ores and collector compositions for use therein which provide an improved grade and recovery. The present disclosure additionally provides an improvement in that there is a reduced need for the addition of a depressant such as lime depressant.

The disclosure provides a process to treat metal or mineral ores wherein the metal or mineral ore is a metallic sulphide ore containing copper, gold, platinum, silver, nickel, molybdenum, arsenic sulphides, cobalt, zinc, lead, tin, antimony or combinations thereof, with a collector composition that includes a dimeric fatty nitrile. The dimeric fatty nitrile has the general formula (I):

where $R_1$, $R_2$, $R_3$ and $R_4$ are saturated or unsaturated, aliphatic or aromatic, linear, cyclic or branched, hydrocarbon groups, each group independently containing between 3 and 14 carbon atoms. Preferably, $R_1$, $R_2$, $R_3$ and $R_4$ are saturated or unsaturated, linear or branched, hydrocarbon groups, each group independently containing between 3 and 14 carbon atoms.

As described herein, degree of unsaturation means the number of carbon-carbon double bonds per one dimeric fatty nitrile. In some embodiments, the degree of unsaturation of the dimeric fatty nitrile is between 0.1 and 0.5. More preferably, the degree of unsaturation is between 0.15 and 0.3.

In some embodiments, the number of carbon atoms in R1+R2+R3+R4 is between 12 and 56. More preferably, the number of carbon atoms in R1+R2+R3+R4 is between 20 and 44. In one particular embodiment, the number of carbon atoms in R1+R2+R3+R4 is 32 or 36.

The collector composition in embodiments contains less than 30 wt %, preferably less than 10 wt %, more preferably less than 5 wt % of dimeric fatty amine on the weight of dimeric fatty nitrile. While such amines are suitable for treating non-sulfidic ores when treating metallic sulfide ores it is demonstrated that low amounts of dimeric fatty amines have a negative effect on the flotation process results for such metallic sulfide ores.

The dimeric fatty nitriles described herein are formed by reacting a dimeric fatty acid with ammonia and removing water from the reaction product to form the dimeric fatty nitrile.

Dimeric fatty acids are dicarboxylic acids prepared by the dimerization of (mono- or poly-) unsaturated fatty acids. Common dimeric fatty acids include the dimerization products of tall oil fatty acid, oleic acid, linoleic acid and elaidic acid. The dimeric fatty acid described herein has the general formula (II):

where $R_1$, $R_2$, $R_3$ and $R_4$ are saturated or unsaturated, aliphatic or aromatic, linear, cyclic or branched, hydrocarbon groups, each independently containing between 3 and 14 carbon atoms and correspond to the same $R_x$ groups as the dimeric fatty nitrile product. Preferably, $R_1$, $R_2$, $R_3$ and $R_4$ are saturated or unsaturated, linear or branched, hydrocarbon groups, each group independently containing between 3 and 14 carbon atoms. Commercially available dimeric fatty acids are typically a mixture of dimeric, monomeric and trimeric fatty acids. Preferably, the dimeric fatty acid used according to the instant disclosure has a dimer content of at least 90% by weight.

To form the dimeric fatty nitrile, the dimeric fatty acid is reacted with ammonia ($NH_3$) to form a dimeric fatty amide via an ammoniation reaction. The dimeric fatty amide is then dehydrated to produce the dimeric fatty nitrile. It is believed the reaction proceeds as shown below:

The ammoniation reaction (A) can be carried out at a temperature between about 200° C. and about 400° C. and at a pressure between about 0 KPa (0 atm) and about 507 KPa (5 atm). In other embodiments, the ammoniation reaction (A) is carried out at a temperature between about 250° C. and about 350° C. and at a pressure between about 100 KPa (1 atm) and about 304 KPa (3 atm).

The dehydration reaction (B) can also be carried out at a temperature between about 200° C. and about 400° C. and at a pressure between about 0 KPa (0 atm) and about 507 KPa (5 atm). In other embodiments, the dehydration reaction (B) is carried out at a temperature between about 250° C. and about 350° C. and at a pressure between about 100 KPa (1 atm) and about 304 KPa (3 atm). The dehydration reaction (B) conditions can be the same as or different from the ammoniation reaction (A) conditions.

The ammoniation reaction (A) can occur in the presence of a catalyst. Preferably, the catalyst is a metal oxide catalyst. Suitable metal oxide catalysts include zinc oxide (ZnO), cobalt oxide (CoO) and combinations thereof. In some embodiments, the catalyst is ZnO and is present at a concentration between about 0.001% by weight and about 0.2% by weight relative to the amount of the dimeric fatty acid. In other embodiments, the catalyst is CoO and is present at a concentration between about 0.001% by weight and about 0.2% by weight relative to the amount of the dimeric fatty acid. The dehydration reaction (B) can also occur in the presence of the catalyst used in the ammoniation reaction (A).

During the ammoniation reaction (A), ammonia is flowed to a reactor containing the dimeric fatty acid and catalyst. The flow of ammonia can be between about 0.1 moles per hour per mole of dimeric fatty acid and about 5 moles per hour per mole of dimeric fatty acid. In some embodiments, the flow of ammonia is between about 0.2 moles per hour per mole of dimeric fatty acid and about 2 moles per hour per mole of dimeric fatty acid. During the dehydration reaction (B), the flow of ammonia can continue at the same conditions of the ammoniation reaction (A). Alternatively, another gas can be flowed to the reactor or a vacuum can be applied to the reactor to form the dimeric fatty nitrile.

In some embodiments, the dimeric fatty nitrile is prepared as described in U.S. Patent Application Publication No. 2011/0190541.

It should be noted that the dimeric fatty nitrile preparation process in preferred embodiments does not contain a step in which the nitrile groups of the dimeric fatty nitrile are subjected to a hydrogenation step. Some—very limited—conversion of the nitrile to the amine may still find place unintendedly, especially when hydrogen is present. Accordingly, in the dimeric fatty nitrile in embodiments less than 30 wt % of dimeric fatty amine is present, preferably less than 10 wt % and more preferably less than 5 wt % on total dimeric fatty nitrile weight.

The disclosure furthermore provides collector compositions containing as component (a) 1 wt % to 99 wt % of a nitrile group-containing compound of the formula (I):

where $R_1$, $R_2$, $R_3$ and $R_4$ are saturated or unsaturated, aliphatic or aromatic, linear, cyclic or branched, hydrocarbon groups, preferably, saturated or unsaturated, linear or branched, hydrocarbon groups, each group independently containing between 3 and 14 carbon atoms, and as component (b) 1 to 99 wt % of at least one of a collector selected from the group of nitrile, xanthate, dithiophosphate, thionocarbamate, thiocarbamate, mercaptobenzylthiazole, alkynes, monothiophosphate and dithiophosphinates and hydroxamate collectors, or a frother selected from the group of phenols, alkyl sulfates, aliphatic alcohols, generally C5-C8 cyclic alcohols, alkoxyalkanes, polypropylene glycol ethers, polyglycol ethers, polyglycol glycerol ethers, pyridine base, natural oils such as terpineol (as in pine oil) and cresols, mixed ethers, aldehydes and ketone co-products of oxo alcohol production, and ethoxylated alcohols.

In a preferred embodiment, the composition contains component (a) in an amount of 5 to 95 wt % and component (b) in an amount of 5 to 95 wt %.

The process of the disclosure can be a direct or reverse flotation process. For example, in an ore containing copper sulfide and zinc sulfide the zinc is depressed and the copper is floated off the zinc sulfide. The process is in an embodiment a reverse flotation of zinc sulfide. When copper ore is floated, the process is in an embodiment a direct flotation.

If component (b) in the collector compositions according to the disclosure is a nitrile collector, it should be understood that it is a nitrile compound different from the nitrile-containing compound as component (a). Preferably, component (b) is a xanthate, dithiophosphate, dithiophosphinate, thionocarbamate collector.

The metal or mineral ore is a metallic sulfide ore containing copper, gold, platinum, silver, nickel, molybdenum, arsenic sulfides, cobalt, zinc, lead, tin, antimony, preferably, copper, molybdenum, zinc, lead, gold, platinum, or silver.

The process of the disclosure may involve other additives and auxiliary materials which are typically present in a froth flotation process that can be added at the same time or, preferably, separately during the process. Further additives that may be present in the flotation process are further collectors (such as thiol-based collector, like xanthate, dithiophosphate, thionocarbamate, thiocarbamate, mercaptobenzylthiazole, monothiophosphate and dithiophosphinates and hydroxamate or other nitrile collectors), depressants (such as lime, starch, chromate, cyanide, sodium sulfide, zinc sulfate, sulfur dioxide, sodium hydrosulfide, polysulfides, copper sulfate, bisulfites, metabisulfite, polyphosphates, chromates, starch, cellulose-based reagents), dispersants (such as sodium silicate and poly acrylic acid (PAA)) and activators (such as copper sulfate, sodium sulfide, sodium hydrosulfide), frothers/froth regulators/froth modifiers/defoamers (such as aliphatic alcohols such as MIBC, Flottec FX120-01 and ethyl hexanol, polypropylene glycols and their ethers such as Dowfroth 200, Dowfroth 250, Dowfroth 1012, Flottec FX160-01, FX160-05, F160, F150; polyethylene glycols and their ethers such as FlottecFX120-02, Nassaco MasFroth240 and Sasol NovelFrother 234), and pH-regulators (such as sodium hydroxide, lime or sodium carbonate). In preferred embodiments, lime is used in an amount of about 10 to about 1,000 g/t of ore as a pH modifier and a depressant of iron pyrites In another aspect, the present disclosure relates to a pulp comprising crushed and ground ore, a collector composition as defined herein, and optionally further flotation aids. This pulp can be prepared by first grounding the ore and then adding collector composition or by adding at least part of the collector composition to the ore and milling the ore to pulp in the presence of at least part of the collector composition.

The metallic sulfide ores that can be used in the process of the disclosure may include stibnite, arsenopyrite, bismuthinite, greenockite, cobaltite, carrolite, linnaeite, chalcopyrite, chalcocite, bornite, covellite, tennantite, tetrahedrite, enargite, argyrodite, pyrrhotite, pyrite, galena, jamesonite, cinnabar, molybdenite, penlandite, millerite, heazelwoodite, argentite, acanthite, patronite, sphalerite, wurtzite and marmatite-containing ores.

The amount of the collector used in the process of reversed flotation of the present disclosure will depend on the amount of impurities present in the ore and on the desired separation effect, but in some embodiments will be in the range of from 1-500 g/ton dry ore, preferably in the range of from 5-100 g/ton dry ore, more preferably 5-30 g/ton dry ore.

EXAMPLES

Example 1

Dimeric Fatty Nitrile Synthesis

A dimeric fatty nitrile was prepared according to the procedure described in Example 1 of U.S. Patent Application Publication No. 2011/0190541 except that Pripol™ 1017 (hydrogenated dimer and trimer acid mixture, available from Croda International plc, East Yorkshire, UK) was used as the starting material. The product was analysed by titration and found to possess an acid content of about 0.03-0.04% by weight.

Example 2

Flotation Procedure 500 g of a copper ore containing 0.5% copper and about 20 wt % of pyrite was milled without lime or any gangue suppressant. The milling time was adjusted to produce a product at 80% pass 75 microns ($P_{80}$=75 μm).

The milled ore was placed into a 1.4 L Denver flotation cell. Tap water (naturally containing 22 g/L of calcium) was added to the marked level in the cell (1.4 L) and the mixing started. The ore sample was left at its natural equilibrated pH during milling and flotation. The collector as indicated in Table 1 below (Dimeric fatty nitriles, C18-unsaturated, dimers (as prepared in Example 1) or alkyl-nitrile (Coco)) in an amount of 20 g/t of ore, and frother (methyl isobutyl carbinol (MIBC)) in an amount of 20 g/t of ore were added and conditioned for 3 minutes. The experiments were conducted without lime as a depressant. The rougher flotations followed by two cleaning steps were performed. All the fractions (rougher tailings, middlings and concentrate) were collected and analyzed.

TABLE 1

Treatment of copper ore containing about 20% iron pyrite with several collectors without depressant

| Sample | Collector | Collector dose g/t | Frother (MIBC) dose g/t | pH |
|---|---|---|---|---|
| A | Dimeric fatty nitriles, C18-unsaturated, dimers | 20 | 20 | 7.5-7.9 |
| B (comp) | Alkyl-nitrile (Coco) | 20 | 20 | 7.5-7.9 |

Results

Figure 1:
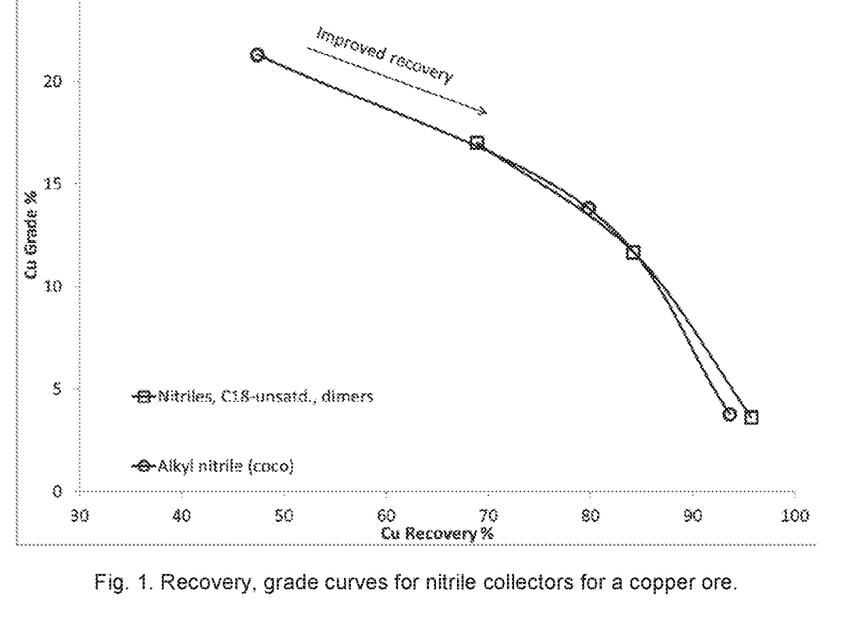
FIG. 1 is a graph showing the recovery grade curves for nitrile collectors for copper ore.

The results are shown in Table 2 and graphically represented in FIG. 1.

TABLE 2

% copper recovered

| Sample | Collector | % recovery Cu |
|---|---|---|
| A | Dimeric fatty nitriles, C18-unsaturated, dimers | 69 |
| B (comp) | Alkyl-nitrile (Coco) | 47 |

The dimeric fatty nitriles, C18-unsaturated, dimers collector performed well for removing copper minerals without the addition of lime depressant. The FIG. 1 shows that the dimeric fatty nitriles, C18-unsaturated, dimers collector had a grade recovery curve as good as, if not better than, the alkyl-nitrile (coco) collector.

Example 3

Flotation Procedure 500 g of a copper ore containing 0.35% copper and about 15% of pyrite and about 2.6 g/t (ppm) of gold was milled without lime or any gangue suppressant for collection with the following collectors: dimeric fatty nitriles, C18-unsaturated, dimers and potassium amyl xanthate (PAX). Lime depressant was used with potassium amyl xanthate (PAX), as is conventional in the industry to suppress the flotation of pyrite gangue. The milling time was adjusted to produce a product at 80% pass 75 microns (P80=75 μm).

The milled ore was placed into a 1.4 L Denver flotation cell. Tap water (naturally containing 22 g/L of calcium) was added to the marked level in the cell (1.4 L) and the mixing started. The ore sample was left at its natural equilibrated pH during milling and flotation or adjusted to pH10.3 using lime. The collector as indicated in Table 3 below (dimeric fatty nitriles, C18-unsaturated, dimers or PAX) in an amount of 20 g/t of ore, and frother (methyl isobutyl carbinol (MIBC)) in an amount of 20 g/t of ore were added and conditioned for 3 minutes. The experiments were conducted either without (Sample A) or with (Sample B) lime as a depressant. The rougher flotations followed by two cleaning steps were performed. All the fractions (rougher tailings, middlings and concentrate) were collected and analyzed.

TABLE 3

Treatment of copper ore containing about 20% iron pyrite with several collectors without depressant

| Sample | Collector | Collector dose g/t | Frother (MIBC) dose g/t | pH |
|---|---|---|---|---|
| A | Dimeric fatty nitriles, C18-unsaturated, dimers | 20 | 20 | 7.5-7.9 |
| B (comp) | Potassium amyl xanthate (PAX) | 20 | 20 | 10.3 |

Results

Figure 2:
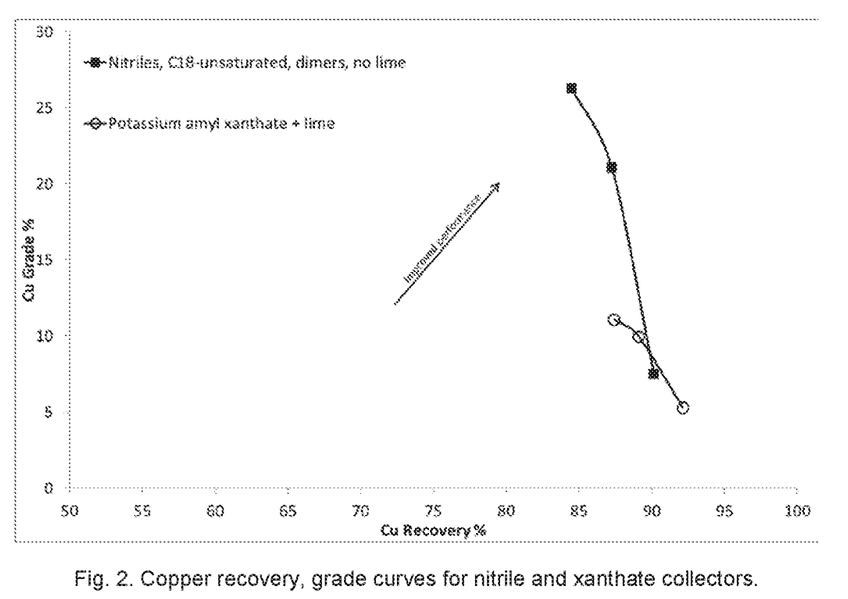
FIG. 2 is a graph showing the copper recovery grade curves for nitrile and xanthate collectors.
Figure 3:
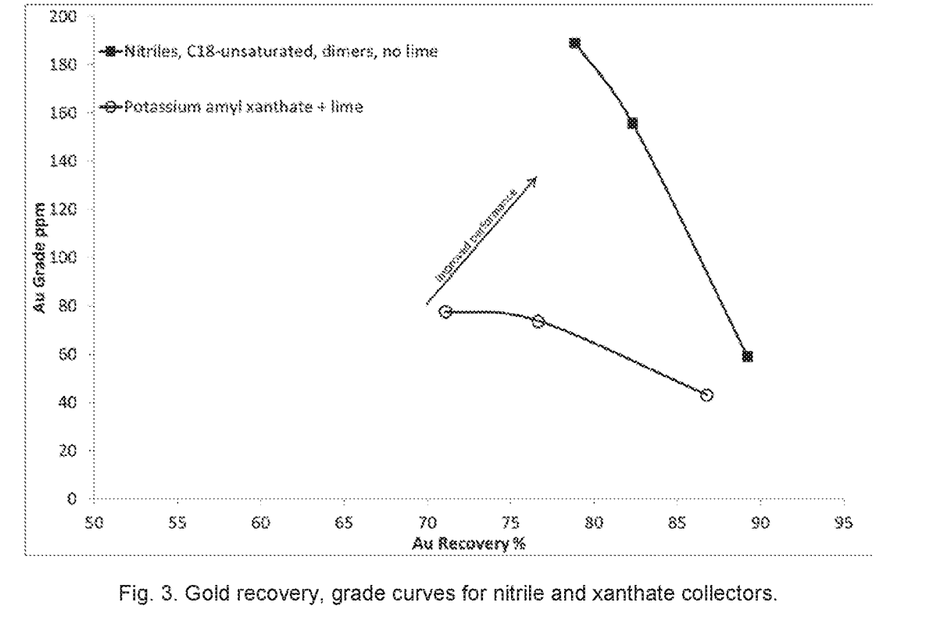
FIG. 3 is a graph showing the gold recovery grade curves for nitrile and xanthate collectors.

The copper and gold results are shown graphically in FIGS. 2 and 3, respectively. The dimeric fatty nitriles, C18-unsaturated, dimers collector had grade recovery curves superior to that of PAX and performed well for removing copper minerals and gold without the addition of lime depressant.

Example 4

Flotation Procedure 500 g of a lead zinc ore containing 1.9% zinc and 1.6% lead and about 5 wt % of pyrite was milled without lime or any gangue suppressant. The milling time was adjusted to produce a product at 80% pass 105 microns (P80=105 μm).

The milled ore was placed into a 1.4 L Denver flotation cell. Tap water (naturally containing 22 g/L of calcium) was added to the marked level in the cell (1.4 L) and the mixing started. The ore sample was left at its natural equilibrated pH during milling and flotation. The collector as indicated in Table 4 below (Dimeric fatty nitriles, C18-unsaturated, dimers or alkyl-nitrile (Coco)) in an amount of 20 g/t of ore, and frother (methyl isobutyl carbinol (MIBC)) in an amount of 20 g/t of ore were added and conditioned for 3 minutes.

The experiments were conducted without lime as a depressant. The rougher flotations followed by two cleaning steps were performed. All the fractions (rougher tailings, middlings and concentrate) were collected and analyzed.

TABLE 4

Treatment of lead zinc ore with several collectors without depressant

| Sample | Collector | Collector dose g/t | Frother (MIBC) dose g/t | pH |
|---|---|---|---|---|
| A | Dimeric fatty nitriles, C18-unsaturated, dimers | 20 | 20 | 7.5-7.9 |
| B (comp) | Alkyl-nitrile (Coco) | 20 | 20 | 7.5-7.9 |

Results

Figure 4:
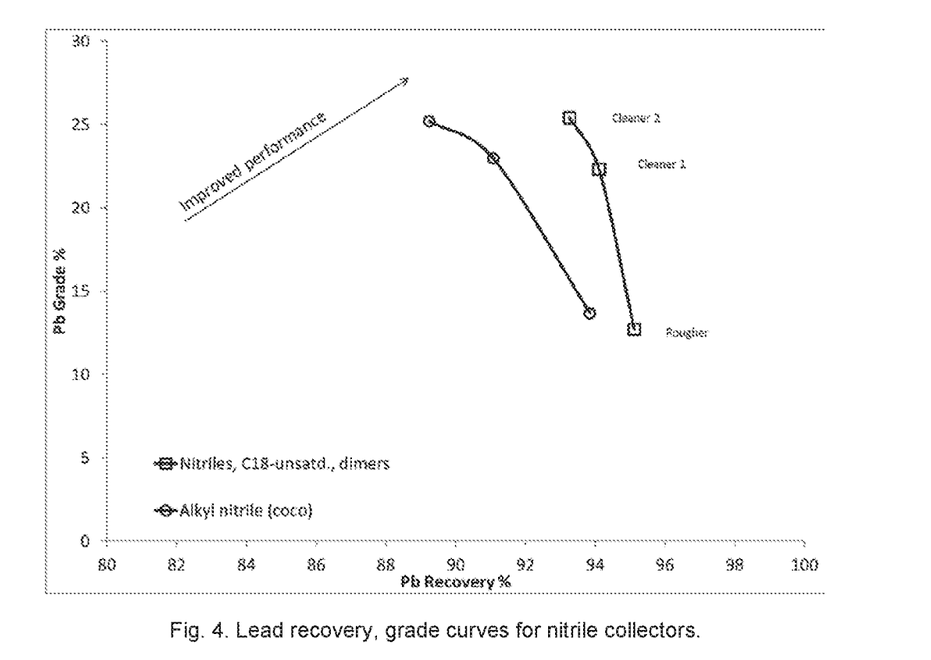
FIG. 4 is a graph showing the lead recovery grade curves for nitrile collectors.
Figure 5:
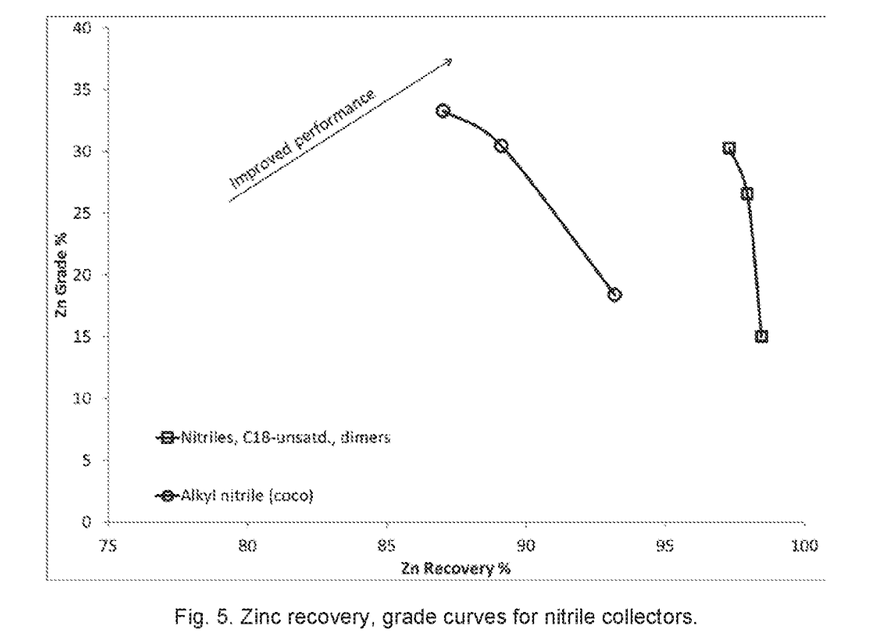
FIG. 5 is a graph showing the zinc recovery grade curves for nitrile collectors.

The lead and zinc results are shown graphically in FIGS. 4 and 5, respectively. The dimeric fatty nitriles, C18-unsaturated, dimers collector had grade recovery curves superior to that ok alkyl-nitrile (coco) and performed well for removing lead and zinc minerals without the addition of lime depressant.

Example 5

Effect of hydrogenation of nitriles (to give dimeric fatty amines) when used in collector composition for sulfidic ores.

Flotation Procedure 500 g of a copper ore containing 0.28% copper and about 3% of pyrite was milled without lime or any gangue suppressant for collection with 2 mixed collectors of dimeric fatty amines, C18-unsaturated and dimeric fatty nitriles, C18-unsaturated at 3 ratios: 100:0, 10:90, 0:100. The milling time was adjusted to produce a product at 80% pass 45 microns (P80=45 μm).

The milled ore was placed into a 1.4 L Denver flotation cell. Tap water (naturally containing 22 g/L of calcium) was added to the marked level in the cell (1.4 L) and the mixing started. The ore sample was left at its natural equilibrated pH during milling and flotation. Each flotation used a total amount of collector of 15 g/t of ore, and frother (methyl isobutyl carbinol (MIBC)) in an amount of 60 g/t of ore were added and conditioned for 3 minutes. The rougher flotations followed by two cleaning steps were performed. All the fractions (rougher tailings, middlings and concentrate) were collected and analyzed.

Results

Figure 6:
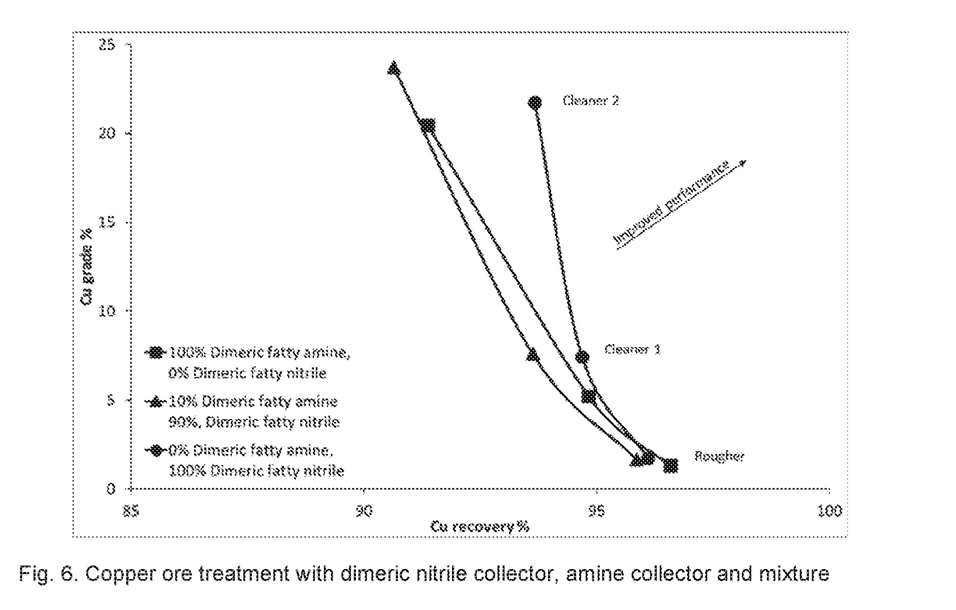
FIG. 6 is a graph showing the recovery grade curves from copper ore treatment with a dimeric nitrile collector, an amine collector, and mixture thereof.

The results are shown in FIG. 6.

From the results it can be taken that if dimeric fatty nitriles are hydrogenated into their amines, the performance of the collector when used to treat sulfidic copper ores gets clearly less. Already when 10% of the nitriles are replaced with amines, the performance is significantly less.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A method to treat metal or mineral ores, wherein the metal or mineral ore is a metallic sulphide ore including copper, gold, platinum, silver, nickel, molybdenum, arsenic, cobalt, zinc, lead, tin, antimony, or combinations thereof with a collector composition comprising a dimeric nitrile, wherein the dimeric nitrile is obtainable by a process comprising:
   reacting a dimer fatty acid with ammonia at a temperature between about 200° C. and about 400° C. to form a dimeric amide; and
   removing water from the dimeric amide to form the dimeric nitrile.

2. The method of claim 1 wherein the dimeric nitrile is obtainable by reacting the dimer fatty acid with the ammonia at a pressure between about 0 kPa and about 507 kPa.

3. The method of claim 2 wherein the dimeric nitrile is obtainable by adding the ammonia to a reaction vessel containing the dimer fatty acid at a rate of about 0.1 moles per hour to about 5 moles per hour.

4. The method of claim 2 wherein the dimeric nitrile is obtainable by reacting the dimer fatty acid with the ammonia in the presence of a metal oxide catalyst.

5. The method of claim 1 wherein the dimeric nitrile is obtainable by adding the ammonia to a reaction vessel containing the dimer fatty acid at a rate of about 0.1 moles per hour to about 5 moles per hour.

6. The method of claim 1 wherein the dimeric nitrile is obtainable by reacting the dimer fatty acid with the ammonia in the presence of a metal oxide catalyst.

7. The method of claim 6 wherein the dimeric nitrile is obtainable by using the metal oxide catalyst selected from ZnO, CoO, and combinations thereof.

8. The method of claim 7 wherein the metal oxide catalyst is ZnO, and wherein the ZnO has a concentration relative to the dimer fatty acid of about 0.001% by weight to about 0.2% by weight.

9. The method of claim 8 wherein the dimer fatty acid includes from 12 to 60 carbon atoms.

10. The method of claim 9 wherein the dimer fatty acid includes from 24 to 48 carbon atoms.

11. The method of claim 1 wherein the dimer fatty acid includes from 12 to 60 carbon atoms.

12. The method of claim 11 wherein the dimer fatty acid includes from 24 to 48 carbon atoms.

13. The method of claim 1 wherein the dimeric nitrile is obtainable by removing the water from the dimeric amide at a temperature between about 200° C. and about 400° C. under flow of a gas or application of a vacuum.

14. The method of claim 1 wherein the collector composition includes less than about 30 wt % of dimeric amine based on the weight of dimeric fatty nitrile.

15. The method of claim 1 wherein the collector composition additionally includes at least one collector selected from xanthates, dithiophosphates, thionocarbamates, thiocarbamates, mercaptobenzylthiazoles, monothiophosphates, dithiophosphinates, hydroxamates, alkynes, and combinations thereof or a frother selected from phenols, alkyl sulfates, C5-C8 cyclic alcohols, alkoxyalkanes, polypropylene glycol ethers, polyglycol ethers, polyglycol glycerol ethers, pyridine base, natural oils, mixed ethers, ethoxylated alcohols, and combinations thereof.

16. The method of claim 1 wherein the dimeric nitrile has the general formula (I):

(I)

wherein $R_1$, $R_2$, $R_3$, and $R_4$ are saturated or unsaturated, aliphatic or aromatic, linear, cyclic or branched, hydrocarbon groups, each group independently including from 3 to 14 carbon atoms, and wherein the degree of unsaturation of the dimeric nitrile is from about 0.1 to 0.5.

17. The method of claim 1 comprising the steps of:
conditioning, in an aqueous solution, a pulped metallic or mineral ore wherein the metallic or mineral ore is a metallic sulphide ore including copper, gold, platinum, silver, nickel, molybdenum, arsenic, cobalt, zinc, lead, tin, antimony, or combinations thereof to form a mixture;
optionally concentrating the mixture with magnetic separation;
optionally adding a frother to the mixture;
optionally conditioning the mixture with a flotation depressant or flotation activator;
optionally adjusting the pH of the mixture;
adding the collector composition;
optionally adding an additional flotation aid to the mixture; and
performing a froth flotation by introducing air into the mixture and skimming off froth formed therein to recover metals and/or minerals.

18. A collector composition comprising:
as component (a), from 1% by weight to 99% by weight of a dimeric nitrile compound obtainable by a process comprising:
reacting a dimer fatty acid with ammonia at a temperature between about 200° C. and about 400° C. to form a dimeric amide; and
removing water from the dimeric amide to form the dimeric nitrile compound;
wherein the dimeric nitrile compound has the general formula (I):

(I)

wherein $R_1$, $R_2$, $R_3$, and $R_4$ are saturated or unsaturated, aliphatic or aromatic, linear, cyclic or branched, hydrocarbon groups, each group independently including from 3 to 14 carbon atoms, and wherein the degree of unsaturation of the dimeric nitrile compound is from 0.1 to 0.5, and as component (b), from 1% by weight to 99% by weight of a collector selected from xanthates, dithiophosphates, thionocarbamates, thiocarbamates, alkynes, mercaptobenzylthiazoles, monothiophosphates, dithiophosphinates, hydroxamates, and combinations thereof or a frother selected from phenols, alkyl sulfates, C5-C8 cyclic alcohols, alkoxyalkanes, polypropylene glycol ethers, polyglycol ethers, polyglycol glycerol ethers, pyridine base, natural oils, mixed ethers, ethoxylated alcohols, and combinations thereof.

19. The collector composition of claim 18 wherein the dimer fatty acid includes from 12 to 60 carbon atoms, the dimer fatty acid is reacted with the ammonia at a pressure between about 0 kPa and about 507 kPa, the ammonia is added to a reaction vessel containing the dimer fatty acid at a rate of about 0.1 moles per hour to about 5 moles per hour, the dimer fatty acid is reacted with the ammonia in the presence of a metal oxide catalyst, and the water is removed from the dimeric amide at a temperature between about 200° C. and about 400° C. under flow of a gas or application of a vacuum.

20. The collector composition of claim 18 including from 20% by weight to 80% by weight of component (a) and from 20% by weight to 80% by weight of component (b).

* * * * *